US011540843B2

(12) United States Patent
Highlander et al.

(10) Patent No.: US 11,540,843 B2
(45) Date of Patent: *Jan. 3, 2023

(54) HARVESTING CANCELLOUS BONE AND MARROW FROM DISTAL FEMUR, PROXIMAL TIBIA, DISTAL TIBIA, OR CALCANEUS USING BONE PRESS APPARATUS

(71) Applicant: H&M INNOVATIONS, LLC, Wilmington, NC (US)

(72) Inventors: Peter D. Highlander, Bellevue, OH (US); Robert Sean Hensler, Wilmington, NC (US)

(73) Assignee: H&M Innovations, LLC, Wilmington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/916,099

(22) Filed: Jun. 29, 2020

(65) Prior Publication Data

US 2020/0405911 A1 Dec. 31, 2020

Related U.S. Application Data

(63) Continuation-in-part of application No. PCT/US2020/040037, filed on Jun. 28, 2020.

(Continued)

(51) Int. Cl.
*A61B 17/16* (2006.01)
*A61M 1/00* (2006.01)
(Continued)

(52) U.S. Cl.
CPC .......... *A61B 17/1635* (2013.01); *A61B 17/16* (2013.01); *A61B 17/164* (2013.01);
(Continued)

(58) Field of Classification Search
CPC ... A61B 17/19; A61B 17/1635; A61B 17/164; A61B 17/8897; A61B 2017/1602;
(Continued)

(56) References Cited

U.S. PATENT DOCUMENTS 6,071,284 A * 6/2000 Fox ..................... A61B 10/0233
606/102
6,387,070 B1 * 5/2002 Marino ............ A61B 17/32002
604/35

(Continued)

FOREIGN PATENT DOCUMENTS

WO 9906813 A1 2/1999

OTHER PUBLICATIONS

International Search Report and Written Opinion, dated Oct. 13, 2020, in international patent application PCT/US2020/040037, 11 pages.

*Primary Examiner* — Eric S Gibson
(74) *Attorney, Agent, or Firm* — Chad D. Tillman; Tillman Wright, PLLC (57) ABSTRACT

Methods of harvesting cancellous bone and bone marrow include extracting loosened cancellous bone and bone marrow—including a liquid component thereof—to a collection container that has a first cup and a suction port to which a suction source is connected. After extraction, the suction source is disconnected and a lid of the collection container is removed and replaced with a lid having a plunger with a press head that is configured to filter the extracted liquid by depressing the plunger toward a bottom of the first cup. The filtered liquid is poured through a suction port into a second cup while depressing the plunger, thereby separating the liquid from a semi-solid mass of cancellous bone that remains. The bone is extracted through a cortical opening in the femur, tibia, or calcaneus, or from an intermedullary (Continued)

canal that is preferably formed by reaming of the tibia using an orthopedic reamer.

20 Claims, 9 Drawing Sheets

Related U.S. Application Data (60) Provisional application No. 62/868,855, filed on Jun. 28, 2019, provisional application No. 62/868,860, filed on Jun. 28, 2019.

(51) Int. Cl.
| | | |
|---|---|---|
| *A61F 2/46* | (2006.01) | |
| *A61L 27/36* | (2006.01) | |
| *A61B 17/00* | (2006.01) | |
| *A61F 2/28* | (2006.01) | |
| *A61B 17/56* | (2006.01) | |

(52) U.S. Cl.
CPC .......... *A61F 2/4601* (2013.01); *A61F 2/4644* (2013.01); *A61L 27/3608* (2013.01); *A61M 1/0062* (2013.01); *A61M 1/79* (2021.05); *A61M 1/815* (2021.05); *A61M 1/84* (2021.05); *A61B 2017/00969* (2013.01); *A61B 2017/564* (2013.01); *A61F 2002/2835* (2013.01); *A61F 2002/4685* (2013.01); *A61F 2310/00359* (2013.01); *A61M 2202/10* (2013.01); *A61M 2205/7545* (2013.01); *A61M 2210/02* (2013.01)

(58) Field of Classification Search
CPC .... A61B 2017/564; A61F 2/46; A61F 2/4601; A61F 2/4644; A61F 2002/4645; A61F 2002/4649; A61F 2002/4685
See application file for complete search history.

(56) References Cited

U.S. PATENT DOCUMENTS

| | | | |
|---|---|---|---|
| 6,981,948 | B2 | 1/2006 | Pellegrino |
| 7,175,336 | B2 * | 2/2007 | Voellmicke ........... A61F 2/4644 |
| | | | 366/160.4 |
| 7,758,556 | B2 * | 7/2010 | Perez-Cruet ............ A61M 1/79 |
| | | | 604/317 |
| 8,845,605 | B2 * | 9/2014 | Hensler .................. A61M 1/79 |
| | | | 604/319 |
| 9,248,077 | B1 | 2/2016 | Kelly et al. |
| 10,039,870 | B2 | 8/2018 | Su |
| 10,231,743 | B2 * | 3/2019 | Nassutt ............. A61B 17/1635 |
| 10,493,183 | B2 * | 12/2019 | Hensler .................. A61M 1/60 |
| 11,000,295 | B2 * | 5/2021 | Seykora .............. A61B 17/164 |
| 11,160,916 | B2 * | 11/2021 | Hensler ............... A61M 1/0001 |
| 2003/0225344 | A1 | 12/2003 | Miller |
| 2004/0117025 | A1 | 6/2004 | Reindel |
| 2004/0167617 | A1 * | 8/2004 | Voellmicke ........... A61F 2/4601 |
| | | | 623/1.23 |
| 2004/0191897 | A1 | 9/2004 | Muschler |
| 2007/0276352 | A1 * | 11/2007 | Crocker ............... A61B 10/025 |
| | | | 604/500 |
| 2010/0298835 | A1 * | 11/2010 | Ralph ..................... A61B 17/17 |
| | | | 606/80 |
| 2011/0230886 | A1 * | 9/2011 | Gustilo ................ A61B 17/164 |
| | | | 606/80 |
| 2011/0262405 | A1 * | 10/2011 | Segina ................ A61L 27/3691 |
| | | | 424/93.7 |
| 2012/0221005 | A1 * | 8/2012 | Corneille ........... A61B 17/1725 |
| | | | 606/62 |
| 2012/0330220 | A1 * | 12/2012 | Hensler .................. A61M 1/60 |
| | | | 604/22 |
| 2015/0090652 | A1 * | 4/2015 | Hensler .................. A61M 1/60 |
| | | | 210/232 |
| 2016/0263571 | A1 * | 9/2016 | Duffy .................... A61B 10/025 |
| 2016/0278790 | A1 * | 9/2016 | Nassutt ............. A61B 17/1635 |
| 2019/0192172 | A1 * | 6/2019 | Nassutt ................ A61B 17/164 |
| 2020/0100800 | A1 * | 4/2020 | Seykora .............. A61B 17/164 |
| 2020/0397449 | A1 * | 12/2020 | Spanyer ............. A61B 17/1664 |
| 2020/0405324 | A1 * | 12/2020 | Highlander ........... A61F 2/4601 |
| 2020/0405911 | A1 * | 12/2020 | Highlander ............. A61M 1/84 |

\* cited by examiner

Case Facts

| | |
|---|---|
| Patient Demographics: | 57F - Triple arthrodesis |
| Harvest Site: | Distal Tibia - Harvest site "back-filled" with gel-foam (no allograft used) |
| Type of Drill: | High-Speed Drill<br>> 4 mm Cutting Burr |
| Technique: | Drill inserted and manipulated within the distal Tibia |
| Cortical Window Creation: | Cancellous bone / Marrow 'clinically' rich site<br>> Drill Method: Highlander Technique<br>> Size of Cortical window: 7 mm<br>> Depth of drilled reeming: 2.3 cm |
| The Collection: | 12 cc Cancellous Autograft<br>10 cc Liquid Bone Marrow |
| O. R. Time: | 7 Mins (skin to skin) |
| Value Propostion: | 1:1 Savings ▲ Autograft: Allograft |
| Patient Benefit: | > Smallest cortical window without sacrificing yield<br>> Use of patients own Mesenchymal stem cells and growth factors for fusion<br>> Significant fiscal savings<br>> No large pilot hole (compared to competitors)<br>> Less disruptive and aggressive than other competitive devices |

HARVESTING CANCELLOUS BONE AND MARROW FROM DISTAL FEMUR, PROXIMAL TIBIA, DISTAL TIBIA, OR CALCANEUS USING BONE PRESS APPARATUS

CROSS-REFERENCE TO RELATED APPLICATION

The present application is a continuation-in-part of, and claims priority under 35 U.S.C. § 120 to, international patent application PCT/US20/40037 designating the United States, filed Jun. 28, 2020, the disclosure of which is incorporated herein by reference, and which international patent application is a U.S. nonprovisional patent application of, and claims priority under 35 U.S.C. § 119(e) to, each of U.S. provisional patent application 62/868,855, filed Jun. 28, 2019, which '855 application is incorporated by reference herein; and U.S. provisional patent application 62/868,860, filed Jun. 28, 2019, which '860 application is incorporated by reference herein. Additionally, the present application is a U.S. nonprovisional patent application of, and claims priority under 35 U.S.C. § 119(e) to, each of U.S. provisional patent application 62/868,855, filed Jun. 28, 2019, which '855 application is incorporated by reference herein; and U.S. provisional patent application 62/868,860, filed Jun. 28, 2019, which '860 application is incorporated by reference herein. The disclosures of the '855 and '860 applications are set forth in the appendices and the computer program listing, all of which is incorporated by reference herein.

COPYRIGHT STATEMENT

Any new and original work of authorship in this document—including any source code—is subject to copyright protection under the copyright laws of the United States and other countries. Reproduction by anyone of this document as it appears in official governmental records is permitted, but otherwise all other copyright rights whatsoever are reserved.

Computer Program Listing

Submitted concurrently herewith via the USPTO's electronic filing system, and incorporated herein by reference, are computer program files including instructions, routines, and/or other contents of several computer programs. A table setting forth the name and size of files included in the computer program listing is included below.

| File Name | Creation Date | File Size (bytes) |
|---|---|---|
| ascify.txt | Jun. 28, 2019 19:26 | 37,473 |
| readme-62868855.txt | Jun. 28, 2019 19:27 | 2,780 |
| one1.txt | Jun. 28, 2019 19:19 | 22478505 |
| one2.txt | Jun. 28, 2019 19:19 | 22478162 |
| one3.txt | Jun. 28, 2019 19:19 | 6004473 |
| readme.txt | Jun. 28, 2019 19:37 | 2,781 |
| two1.txt | Jun. 28, 2019 19:22 | 22478505 |
| two2.txt | Jun. 28, 2019 19:22 | 22478162 |
| two3.txt | Jun. 28, 2019 19:22 | 22477819 |
| two4.txt | Jun. 28, 2019 19:22 | 22477476 |
| two5.txt | Jun. 28, 2019 19:22 | 22477133 |
| two6.txt | Jun. 28, 2019 19:22 | 22476790 |
| two7.txt | Jun. 28, 2019 19:22 | 22476447 |
| two8.txt | Jun. 28, 2019 19:22 | 22476104 |
| two9.txt | Jun. 28, 2019 19:22 | 22475761 |
| two10.txt | Jun. 28, 2019 19:22 | 22475418 |
| two11.txt | Jun. 28, 2019 19:22 | 7518709 |

One of these files, "readme-62868855.txt", contains instructions for extracting information from "one1.txt", "one2.txt", and "one3.txt"; "one1.txt", "one2.txt", and "one3.txt" collectively represent a compressed binary file that has been converted to ascii format. These files can be converted back to a compressed .zip archive utilizing an assembly conversion program source code for which is contained in "ascify.txt". The readme file includes instructions for compiling and running this conversion program, and instructions for converting the other text files to a compressed, binary file. This compressed, binary file includes an .mp4 video file for a video illustrating aspects and features in accordance with one or more preferred embodiments of the invention relating to harvesting autologous cancellous bone and marrow from the proximal tibial.

One of these files, "readme.txt", contains instructions for extracting information using "ascify.txt" from the other .txt files. The other .txt files named "twoX.txt", where X=1 to 11, collectively represent a compressed binary file that has been converted to ascii format. These files can be converted back to a compressed .zip archive utilizing an assembly conversion program source code for which is contained in "ascify.txt". The readme file includes instructions for compiling and running this conversion program, and instructions for converting the other text files to a compressed, binary file. This compressed, binary file includes four .mov video files illustrating aspects and features in accordance with one or more preferred embodiments of the invention.

BACKGROUND OF THE INVENTION

The invention generally relates to methods and apparatus used for harvesting cancellous bone and marrow and, preferably, harvesting autologous cancellous bone and marrow from a distal femur, proximal tibia, distal tibia, or calcaneus of an individual for use as an autograft for that individual; and an intramedullary canal that is formed in a medullary cavity of a bone of an individual for use as an autograft for that individual, which bone of the medullar cavity may be the tibia or the femur.

With regard to harvesting autologous bone, it is known when forming a intermedullary canal by reaming—which is basically done for a medullary nail—that autologous cancellous bone contained on the reamer after withdrawal may be recovered and used, if desired. Additionally with regard to specifically harvesting autologous cancellous bone and marrow, a procedure is known that is used for shallow-core harvesting of cancellous bone and marrow from the posterior superior iliac spine immediately prior to an anterior cervical discectomy/fusion ("ACDF"), wherein the harvested cancellous bone and marrow is used in that individual during the ACDF procedure. The procedure has been nicknamed the "Ray Iliac Procedure" and is disclosed in U.S. patent application Ser. No. 62/868,779 and in Ser. No. 16/916,012, both of which are incorporated herein by reference. The Ray Iliac Procedure is intended for use in the orthopedic surgical field.

The Ray Iliac Procedure is based on a repurposed use of a bone press apparatus as disclosed, for example, in U.S. Pat. No. 8,920,393, which is incorporated herein by reference. Such bone press apparatus are commercially sold by Hensler Surgical Products, LLC, of Wilmington, N.C. The bone press apparatus was designed for harvesting high-speed drilled bone during spinal procedures, which harvested bone was found to be a moldable and malleable matrix that could be reused in the patient to increase fusion healing rates.

While the Ray Iliac Procedure is believed to be adequate for use in harvesting cancellous bone and marrow in conjunction with an ACDF procedure, it is believed that additional improvements can be made in harvesting cancellous bone and bone marrow from other areas of the body by repurposing such bone press apparatus. Such additional improvements are believed to be provided by one or more methods in accordance with one or more aspects and features of the invention, especially when harvesting cancellous bone and bone marrow from condyles of the tibia and femur and from the calcaneous, and when harvesting cancellous bone and bone marrow from an intermedullary canal formed in the tibia or femur.

Indeed, it has been discovered that one or more methods in accordance with one or more aspects and features of the invention result in unexpectedly high yields of cancellous bone and bone marrow, especially when harvested from an intermedullary canal formed in the tibia or femur; and unexpectedly high yield rates of cancellous bone and bone marrow, especially when harvested from the condyles of the tibia and femur and from the calcaneous, and from an intermedullary canal formed in the tibia or femur.

SUMMARY OF THE INVENTION

The invention includes many aspects and features. Moreover, while many aspects and features relate to, and are described in, the context of harvesting from a distal femur, a proximal tibia, a distal tibia, a calcaneus, and an intermedullary canal, the invention is not limited to use only in such areas. For example, it is contemplated that the invention also is applicable to other areas, as will become apparent from the following summaries and detailed descriptions of aspects, features, and one or more embodiments of the invention.

Accordingly, in an aspect of the invention, a method of harvesting cancellous bone and bone marrow comprises the steps of: (a) creating an intermedullary canal, including loosening for extraction cancellous bone and bone marrow along the canal; (b) inserting a suction tube through the intermedullary canal and extracting the loosened cancellous bone and bone marrow along the intermedullary canal through the suction tube, the bone marrow comprising a liquid, the suction tube being attached to a first lid of a collection container, the collection container having a first cup and a suction port to which a suction source is connected; (c) after extracting the cancellous bone and bone marrow, disconnecting the suction source from the suction port of the collection container; (d) removing the first lid of the collection container from the first cup of the collection container; (e) attaching a second lid to the first cup of the collection container, the second lid having a plunger with a press head configured to filter the extracted liquid contained in the first cup; (f) filtering the extracted liquid by depressing the plunger of the second lid toward a bottom of the first cup; and (g) pouring the filtered liquid from the first cup through a suction port into a second cup while depressing the plunger, thereby separating the liquid from a spongy semisolid mass of cancellous bone that remains in the first cup.

In a feature, the step of creating the intermedullary canal is performed using an orthopedic reamer, wherein the method further preferably comprises collecting cancellous bone and bone marrow from the reamer after withdrawing the reamer from the intermedullary canal.

In a feature, the intermedullary canal that is formed begins at a distal end of a tibia and extends along a longitudinal axis of the tibia toward a proximal end of the tibia.

In a feature, extracting the loosened cancellous bone and bone marrow along the intermedullary canal comprises passing the suction tube in and out of the intermedullary canal while spinning the tube with one hand and holding with the other hand the collection container to which the suction tube is attached.

In a feature, extracting the loosened cancellous bone and bone marrow along the intermedullary canal comprises passing the suction tube in and out of the intermedullary canal over a guide wire that extends within the intermedullary canal.

In a feature, the method further comprises pouring or drawing the filtered liquid from the second cup into a syringe and injecting the liquid within an autograft or directly into an operative site to promote healing.

In a feature, the method further comprises leaving the suction apparatus attached to the lid for repeating the harvesting method.

In a feature, no irrigation is performed during the method that would dilute the extracted liquid.

In a feature, the second lid having the plunger additionally comprises a vent, whereby a low pressure is not created within the first cup during pouring of the liquid through the suction port while depressing the plunger.

In yet another feature, no suction is applied to the first cup during depressing of the plunger and pouring of the liquid from the first cup. In this respect, it will be appreciated that while the liquid is poured through a "suction" port in preferred methods of the invention, suction is not actually applied at this port; such reference to this port being a "suction" port refers to the use of this port when the incorporated bone press apparatus is used as originally intended in accordance with the reference initially disclosing such bone press apparatus, namely, U.S. Pat. No. 8,920,393 incorporated by reference above.

In another aspect, a method of harvesting cancellous bone and bone marrow comprises the steps of: (a) creating an opening in cortical bone; (b) accessing through the opening and loosening for extraction cancellous bone and bone marrow; (c) inserting a suction apparatus through the opening and extracting the loosened cancellous bone and bone marrow, the bone marrow comprising a liquid, the suction apparatus being attached to a first lid of a collection container, the collection container having a first cup and a suction port to which a suction source is connected; (d) after extracting the cancellous bone and bone marrow, disconnecting the suction source from the suction port of the collection container; (e) removing the first lid of the collection container from the first cup of the collection container; (f) attaching a second lid to the first cup of the collection container, the second lid having a plunger with a press head configured to filter the extracted liquid contained in the first cup; (g) filtering the extracted liquid by depressing the plunger of the second lid toward a bottom of the first cup; and (h) pouring the filtered liquid from the first cup through a suction port into a second cup while depressing the plunger, thereby separating the liquid from a spongy semisolid mass of cancellous bone that remains in the first cup.

In a feature, the suction apparatus comprises a suction wand, and extracting the loosened cancellous bone and bone marrow preferably comprises sweeping a distal end of the suction wand in various directions while extracting the loosened cancellous bone and bone marrow, wherein the sweeping step is performed while holding the collection container to which the suction apparatus is attached.

In a feature, the method further comprises pouring or drawing the filtered liquid from the second cup into a syringe and injecting the liquid within an autograft or directly into an operative site to promote healing.

In a feature, the method further comprises leaving the suction apparatus attached to the lid for repeating the harvesting method.

In a feature, no irrigation is performed that would dilute the extracted liquid.

In a feature, no suction is applied to the first cup during depressing of the plunger.

In a feature, the step of creating an opening in cortical bone comprises using a high-speed drill having a cutting burr to create the opening. The cutting burr preferably is used to create the opening and to loosening the cancellous bone and bone marrow for extraction that is accessed through the opening. The cutting burr preferably is a 4 mm cutting burr or a 5 mm cutting burr. (As used herein, "burr" and "bur and interchangeable and intended to mean the same thing.)

In a feature, the step of creating an opening in cortical bone comprises using a drill comprising a 4 mm cutting burr followed by replacing the 4 mm cutting burr with a 5 mm cutting burr and continuing to use the drill.

In a feature, the method preferably comprises using 6 mm and then 7 mm currettes to increase the size of the opening when a large amount of cancellous bone and bone marrow is needed.

In a feature, a maximum dimension of the opening created is approximately 6 mm to 7 mm.

In a feature, a drill is used and the depth of drilling is between 1.8 cm to 2.3 cm inclusive.

In yet another feature, 8 cc to 12 cc of cancellous bone and 10 cc to 15 cc of bone marrow is obtained within 8 minutes.

Another aspects relate to a method of harvesting, from an individual, in an operating room and within 8 minutes, at least 8 cc to 12 cc of a spongy semi-solid mass of cancellous bone of the individual and, separated therefrom, at least 10 cc to 15 cc of liquid bone marrow of the individual. The method comprises: (a) using a high-speed drill having a cutting burr to create a cortical window in cortical bone; (b) further using the high-speed drill to loosen for extraction cancellous bone and bone marrow accessed through the cortical window; (c) inserting a suction apparatus through the cortical window and extracting the loosened cancellous bone and bone marrow, the bone marrow comprising a liquid, the suction apparatus being attached to a first lid of a collection container, the collection container having a first cup and a suction port to which a suction source is connected; (d) after extracting the cancellous bone and bone marrow, disconnecting the suction source from the suction port of the collection container; (e) removing the first lid of the collection container from the first cup of the collection container; (f) attaching a second lid to the first cup of the collection container, the second lid having a plunger with a press head configured to filter the extracted liquid contained in the first cup; (g) filtering the extracted liquid by depressing the plunger of the second lid toward a bottom of the first cup; and (h) pouring the filtered liquid from the first cup through a suction port into a second cup while depressing the plunger, thereby separating the liquid from a spongy semi-solid mass of cancellous bone that remains in the first cup.

In a feature, the cortical window is created in cortical bone at a distal tibia.

In a feature, the cortical window is created in cortical bone at a distal femur.

In a feature, the cortical window is created in cortical bone at a proximal tibia.

In a feature, the cortical window is created in cortical bone at a calcaneus.

In another aspect, a method comprises the steps of using a drill to create a cortical window in cortical bone and fragment trabecular bone under the cortical window; inserting a suction apparatus through the cortical window and sweeping the distal ends of the suction apparatus in various directions to extract by suction cancellous bone and bone marrow of the fragmented trabecular bone, the suction apparatus being attached to a collection container to which as suction source is connected; disconnecting the suction source from the collection container; removing a lid of the collection container from a cup of the collection container, to which lid the suction apparatus is attached; attaching a second lid having a plunger with press head for filtering cancellous bone from bone marrow; depressing the plunger and compacting the cancellous bone against the bottom of the cup; and pouring bone marrow from the cup into another cup while depressing the plunger against the cancellous bone, thereby separating the bone marrow from the cancellous bone.

In a feature, the suction apparatus comprises a suction wand.

In a feature, the cortical bone is of the distal femur, proximal tibia, distal tibia, or calcaneus of an individual.

In a feature, the sweeping step is performed while holding the collection container to which the suction apparatus is attached.

In a feature, the method further comprises pouring or drawing bone marrow into a syringe and injecting the drawn bone marrow within the harvested bone graft or directly into an operative site to promote healing.

In a feature, the method further comprises leaving the suction apparatus attached to the lid for repeating harvesting using another cup.

Other aspects comprise methods disclosed herein for harvesting cancellous bone and marrow.

Another aspect comprises a method includes steps for harvesting cancellous bone and marrow and, preferably, harvesting autologous cancellous bone and marrow from a distal femur, proximal tibia, distal tibia, or calcaneus of an individual for use as an autograft for that individual.

Another aspect comprises a method includes steps for harvesting cancellous bone and marrow and, preferably, harvesting autologous cancellous bone and marrow from an intramedullary canal that is formed in a medullary cavity of a bone of an individual for use as an autograft for that individual, which bone of the medullar cavity preferably is the tibia or the femur.

Another aspect comprises apparatus that are used to perform the methods disclosed herein.

Additional aspects and features are disclosed in the appendices, the disclosures of which are incorporated herein by reference, including the disclosures and teachings of the videos.

In addition to the aforementioned aspects and features of the invention, it should be noted that the invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the invention now will be described in detail with reference to the accompanying drawings.

DETAILED DESCRIPTION

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once but not necessarily every time during performance of the claimed method.

Furthermore, it is important to note that, as used herein, "comprising" is open-ended insofar as that which follows such term is not exclusive. Additionally, "a" and "an" each generally denotes "at least one" but does not exclude a plurality unless the contextual use dictates otherwise. Thus, reference to "a picnic basket having an apple" is the same as "a picnic basket comprising an apple" and "a picnic basket including an apple", each of which identically describes "a picnic basket having at least one apple" as well as "a picnic basket having apples"; the picnic basket further may contain one or more other items beside an apple. In contrast, reference to "a picnic basket having a single apple" describes "a picnic basket having only one apple"; the picnic basket further may contain one or more other items beside an apple. In contrast, "a picnic basket consisting of an apple" has only a single item contained therein, i.e., one apple; the picnic basket contains no other item.

When used herein to join a list of items, "or" denotes "at least one of the items" but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers"; the picnic basket further may contain one or more other items beside cheese and crackers.

When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese"; the picnic basket further may contain one or more other items beside cheese and crackers.

The phrase "at least one" followed by a list of items joined by "and" denotes an item of the list but does not require every item of the list. Thus, "at least one of an apple and an orange" encompasses the following mutually exclusive scenarios: there is an apple but no orange; there is an orange but no apple; and there is both an apple and an orange. In these scenarios if there is an apple, there may be more than one apple, and if there is an orange, there may be more than one orange. Moreover, the phrase "one or more" followed by a list of items joined by "and" is the equivalent of "at least one" followed by the list of items joined by "and".

Referring now to the drawings, one or more preferred embodiments of the invention are next described. The following description of one or more preferred embodiments is merely exemplary in nature and is in no way intended to limit the invention, its implementations, or uses.

Generally described, preferred methods of harvesting cancellous bone and bone marrow include extracting loosened cancellous bone and bone marrow—including a liquid component thereof—to a collection container that has a first cup and a suction port to which a suction source is connected. After suctioning, the suction source is disconnected and a lid of the collection container is removed and replaced with a lid having a plunger with a press head that is configured to filter the extracted liquid by depressing the plunger toward a bottom of the first cup. The filtered liquid is poured through a suction port into a second cup while depressing the plunger, thereby separating the liquid from a semi-solid mass of cancellous bone that remains. The bone is extracted through a cortical opening in the femur, tibia, or calcaneus, and preferably from a condyle; however, in other preferred methods the cone is extracted from an intermedullary canal that is formed by reaming of the tibia or femur using an orthopedic reamer.

Figure 1:
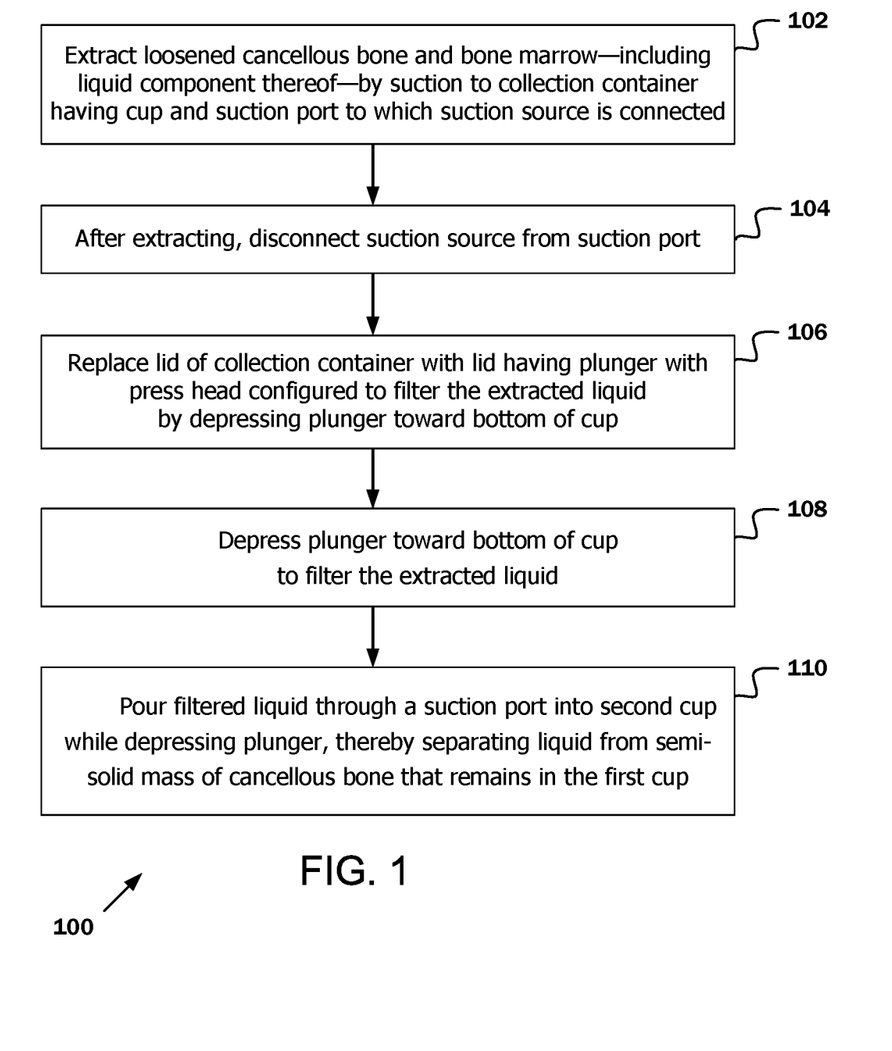
FIG. 1 is a flow chart of a preferred method of harvesting cancellous bone and bone marrow in accordance with one or more aspects and features of the invention.

Accordingly, FIG. 1 is a flow chart of an exemplary preferred method 100 of harvesting cancellous bone and bone marrow in accordance with one or more aspects and features of the invention. This preferred method is used to harvest such bone from the distal femur, proximal tibia, distal tibia, or calcaneous. The method 100 comprises steps 102 through 110. Step 102 comprises extracting loosened cancellous bone and bone marrow—including a liquid component thereof—by suction to a collection container having a cup and a suction port to which a suction source is connected. Step 104 comprises, after step 102, disconnecting the suction source from the suction port. Step 106 comprises replacing a lid of collection container with a lid having a plunger with a press head that is configured to filter the extracted liquid by depressing the plunger toward a bottom of the cup. Step 108 comprises depressing the plunger toward the bottom of the cup to filter the extracted liquid. Step 110 comprises pouring the filtered liquid from the first cup through a suction port into a second cup while depressing the plunger, thereby separating the liquid from a semi-solid mass of cancellous bone that remains in the first cup.

The suction port through which the liquid is poured in step 110 may be part of the first cup or may be part of the lid having the plunger; in the former case, the suction port to which the suction source is attached when performing step 102 is the suction port through which the liquid is poured in subsequent step 110, and in the latter case, the suction port to which the suction source is attached when performing step 102 is a suction port of the first lid, which first lid is replaced in step 106 by the second lid having the plunger. Moreover, it will be appreciated that the former case represents a modification to the cup design of the incorporated bone press apparatus, in which apparatus the cup itself does not include a suction port.

Figure 2:
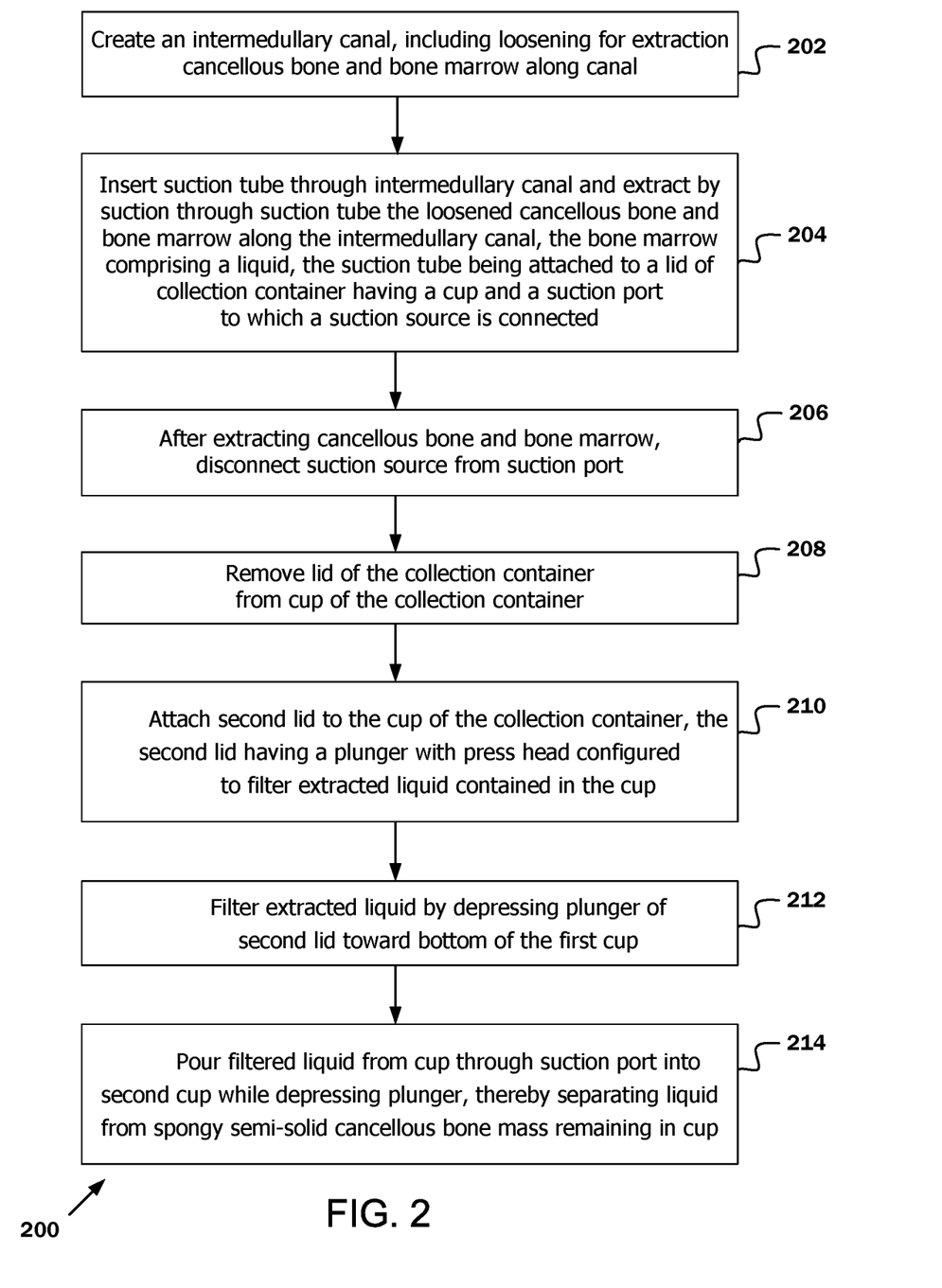
FIG. 2 is a flow chart of another preferred method of harvesting cancellous bone and bone marrow in accordance with one or more aspects and features of the invention.

FIG. 2 is a flow chart of another preferred method 200 of harvesting cancellous bone and bone marrow in accordance with one or more aspects and features of the invention. This preferred method is used to harvest such bone from an intermedullary canal formed in a medullary cavity. The method 200 comprises steps 202 through 214. Step 202 comprises creating within a medullary cavity an intermedullary canal, including loosening for extraction cancellous bone and bone marrow along the intermedullary canal. Step 204 comprises inserting a suction tube through the intermedullary canal and extracting by suction through the suction tube the loosened cancellous bone and bone marrow along the intermedullary canal, wherein the bone marrow comprises a liquid, and wherein the suction tube is attached to a lid of a collection container having a cup and a suction port to which a suction source is connected. Step 206 comprises, after extracting the cancellous bone and bone marrow, disconnecting the suction source from the suction port. Step 208 comprises removing the lid of the collection container from the cup of the collection container. Step 210 comprises attaching a second lid to the cup of the collection container, the second lid having a plunger with a press head that is configured to filter the extracted liquid contained in the cup. Step 212 comprises filtering the extracted liquid by depressing the plunger of the second lid toward a bottom of the cup. Step 214 comprises pouring the filtered liquid from the cup through a suction port into another cup while depressing the plunger, thereby separating the liquid from a spongy semi-solid cancellous bone mass that remains in the cup.

The suction port through which the liquid is poured in step 214 may be part of the first cup or may be part of the lid having the plunger; in the former case, the suction port to which the suction source is attached when performing step 204 is the suction port through which the liquid is poured in subsequent step 214, and in the latter case, the suction port to which the suction source is attached when performing step 204 is a suction port of the first lid, which first lid is replaced in steps 208 and 210 by the second lid having the plunger. Moreover, it will be appreciated that the former case represents a modification to the cup design of the incorporated bone press apparatus, in which apparatus the cup itself does not include a suction port.

Figure 3:
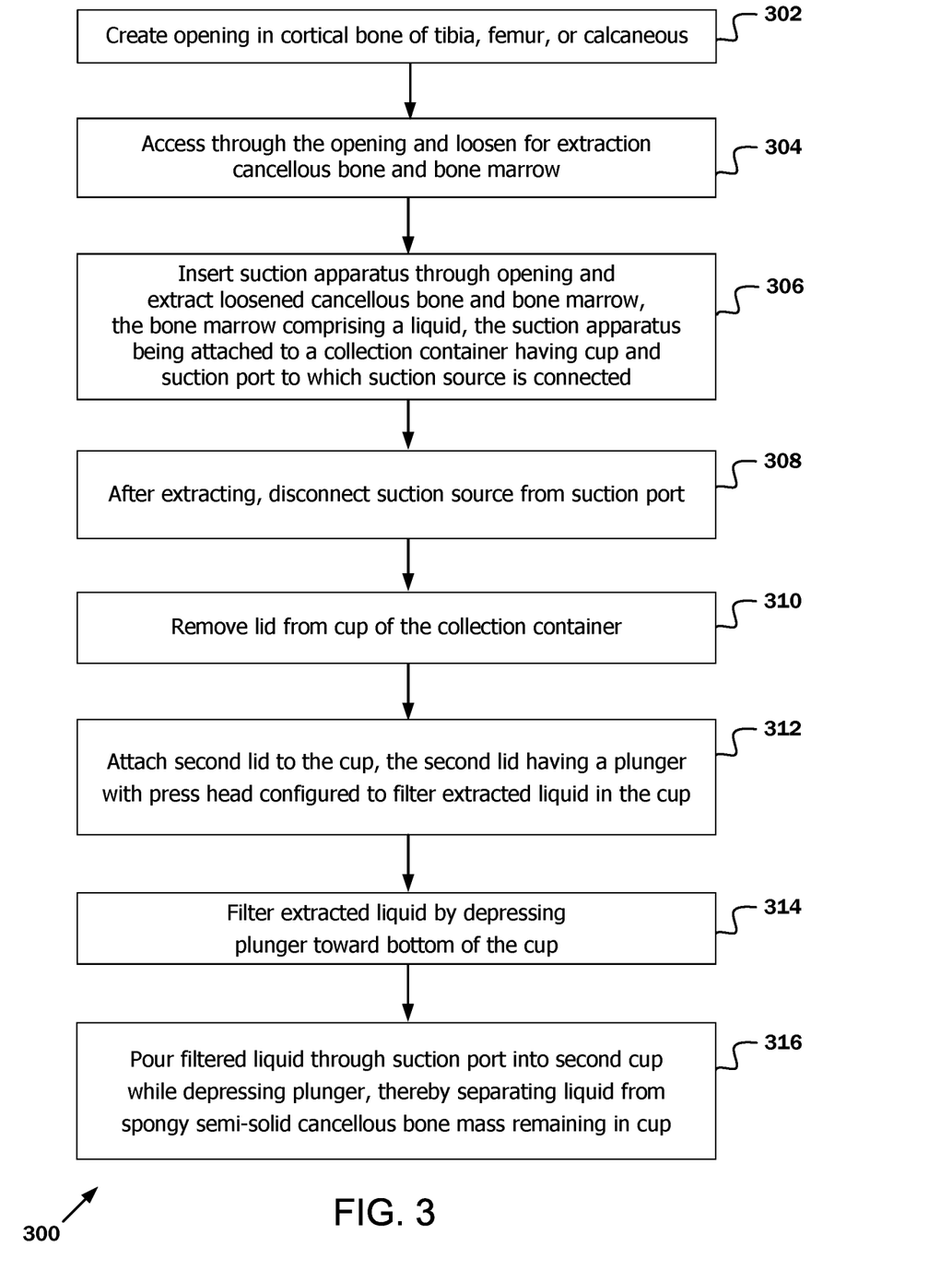
FIG. 3 is a flow chart of another preferred method of harvesting cancellous bone and bone marrow in accordance with one or more aspects and features of the invention.

FIG. 3 is a flow chart of another preferred method 300 of harvesting cancellous bone and bone marrow in accordance with one or more aspects and features of the invention. This preferred method is used to harvest such bone from the distal femur, proximal tibia, distal tibia, or calcaneous. The method 300 comprises steps 302 through 316. Step 302 comprises creating an opening in cortical bone. The opening preferably is made using a circular cutting burr, but other methods of creating an opening can in cortical bone may be used within the scope of the invention, such as first drilling holes and then creating an opening with a hammer and osteotome. One or more curettes also may be used to further expand the opening or round out the opening. Step 304 comprises accessing through the opening and loosening for extraction cancellous bone and bone marrow. Preferably the cutting burr also is used to perform such loosening. Step 306 comprises inserting a suction apparatus through the opening and extracting the loosened cancellous bone and bone marrow, wherein the bone marrow comprises a liquid and the suction apparatus is attached to a collection container having cup and a suction port to which a suction source is connected. Step 308 comprises, after extracting, disconnecting the suction source from the suction port of the collection container. Step 310 comprises removing the lid from the cup of the collection container, and step 312 comprises attaching another lid to the same cup, wherein the second lid has a plunger with a press head that is configured to filter the extracted liquid contained in the cup. Step 314 comprises filtering the extracted liquid by depressing the plunger toward a bottom of the cup. Step 316 comprises pouring the filtered liquid from the cup through a suction port into another cup while depressing plunger, thereby separating the liquid from a spongy semi-solid cancellous bone mass that remains in the first cup.

The suction port through which the liquid is poured in step 316 may be part of the first cup or may be part of the lid having the plunger; in the former case, the suction port to which the suction source is attached when performing step 306 is the suction port through which the liquid is poured in subsequent step 316, and in the latter case, the suction port to which the suction source is attached when performing step 306 is a suction port of the first lid, which first lid is replaced in steps 310 and 312 by the second lid having the plunger. Moreover, it will be appreciated that the former case represents a modification to the cup design of the incorporated bone press apparatus, in which the cup does not have a suction port.

Figure 4:
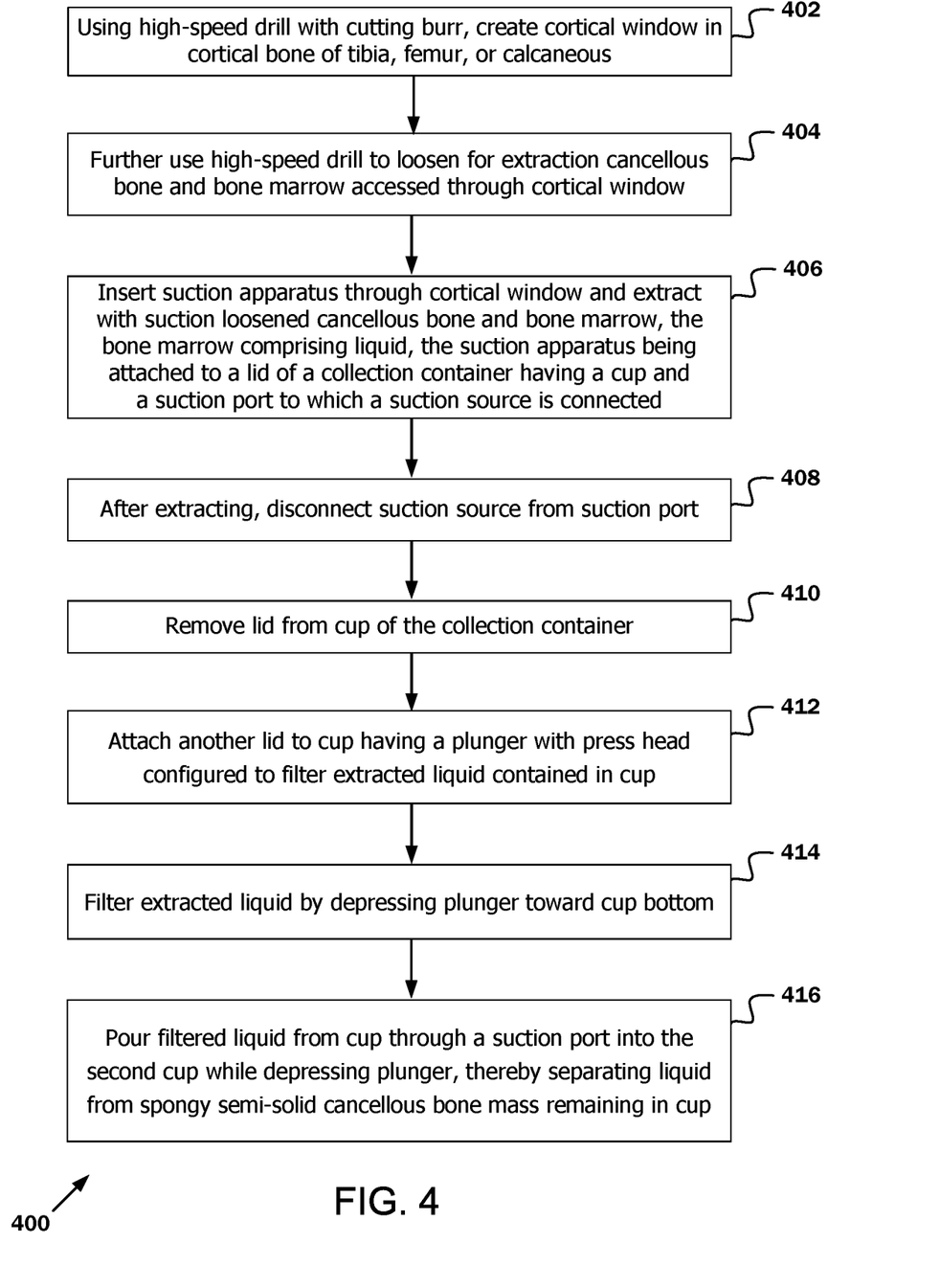
FIG. 4 is a flow chart of another preferred method of harvesting cancellous bone and bone marrow in accordance with one or more aspects and features of the invention.

FIG. 4 is a flow chart of a preferred method 400 of harvesting from an individual, in an operating room and within 8 minutes, at least 8 cc to 12 cc of a spongy semi-solid mass of cancellous bone of the individual and, separated therefrom, at least 10 cc to 15 cc of liquid bone marrow of the individual, all in accordance with one or more aspects and features of the invention. This preferred method is used to harvest such bone from the distal femur, proximal tibia, distal tibia, or calcaneous. The method 400 comprises steps 402 through 416. Step 402 comprises using a high-speed drill with a cutting burr to create a cortical window in cortical bone. Step 404 comprises further using the high-speed drill to loosen for extraction cancellous bone and bone marrow accessed through the cortical window. Step 406 comprises inserting a suction apparatus through the cortical window and extracting with suction the loosened cancellous bone and bone marrow, the bone marrow comprising a liquid, and the suction apparatus being attached to a lid of a collection container having a cup and a suction port to which a suction source is connected. Step 408 comprises, after extracting, disconnecting the suction source from the suction port. Step 410 comprises removing the lid from the cup. Step 412 comprises attaching another lid to the cup which lid has a plunger with a press head that is configured to filter extracted liquid contained in cup. Step 414 comprises filtering the extracted liquid by depressing the plunger toward a bottom of the cup. Step 416 comprise pouring filtered liquid from the cup through a suction port into a second cup while depressing plunger, thereby separating the liquid from a spongy semi-solid cancellous bone mass that is left remaining in the first cup.

The suction port through which the liquid is poured in step 416 may be part of the first cup or may be part of the second lid having the plunger; in the former case, the suction port to which the suction source is attached when performing step 406 is the suction port through which the liquid is poured in subsequent step 416, and in the latter case, the suction port to which the suction source is attached when performing step 406 is a suction port of the first lid, which first lid is replaced in steps 410 and 412 by the second lid having the plunger. Moreover, it will be appreciated that the former case represents a modification to the cup design of the incorporated bone press apparatus, in which apparatus the cup itself does not include a suction port.

Figure 5:
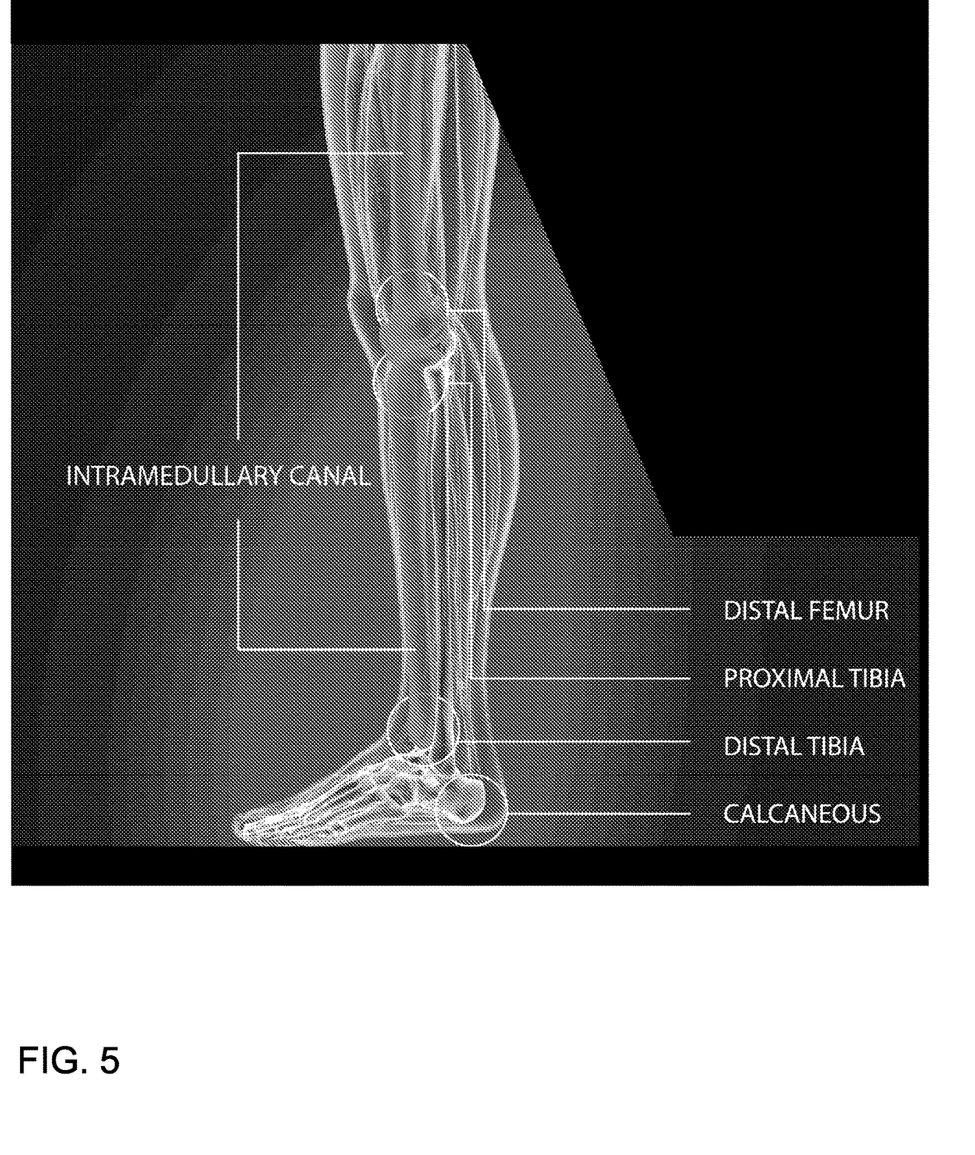
FIG. 5 is a perspective view of a leg illustrating locations for harvesting of bone of one or more preferred methods in accordance with one or more aspects and features of the invention.

With reference now to U.S. patent application publication 2020/0405911 ("the '911 Publication"), which is incorporated herein by reference, the incorporated components of the bone press apparatus that are utilized in preferred methods are perhaps best shown in FIG. 5 of the '911 Publication. The components comprise a first cup 502 with a first lid 504 attached thereto, and a second cup 506 with a second lid 508 attached thereto. The second lid 508 comprises a plunger 510 having a press head for filtering liquid from cancellous bone and a suction port 512. The first lid 504 also includes a suction port 514 and another port 516 for connection to a suction apparatus or suction tube. The cups 502,506 in the bone press apparatus are substantially identical and interchangeable with each other. The bone press apparatus also includes an optional elbow connector 524.

A preferred suction tube 518 is shown in FIG. 6 of the '911 Publication, and a suction apparatus comprising a suction wand 520 is shown in FIG. 7 of the '911 Publication. The suction tube 518 preferably is used to connect the suction wand 520 to the port 516 of the first lid 504 in certain preferred methods of the invention that include harvesting of bone from the distal femur, proximal tibia, distal tibia, and calcaneous, all of which areas are identified in FIG. 5.

Additionally, the suction tube 518 may be cut at desired length forming a distal end thereof for passing the distal end of the suction tube 518 within an intermedullary canal when harvesting bone from the intermedullary canal, in which case the suction wand 520 is not used. In this respect, FIG. 8 of the '911 Publication also illustrates intermedullary canals formed in the tibia and femur.

Figure 9:
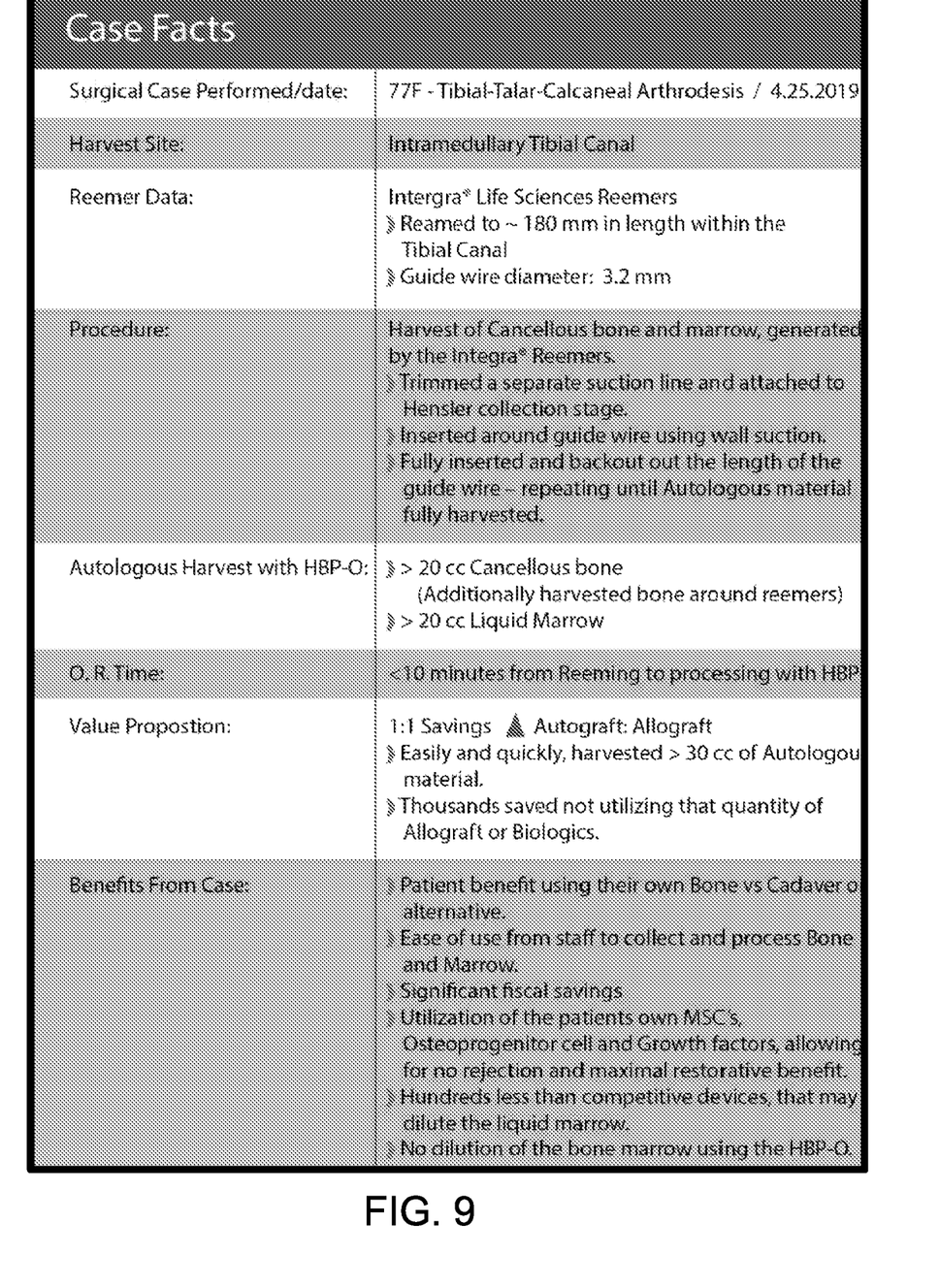
FIG. 9 is a table of case facts relating to the preferred harvesting of the invention performed in connection with the drilling, reaming, inserting, suctioning, and pouring shown respectively in FIGS. 15, 16, 18, 19, and 20 of the '911 Publication.

FIG. 9 of the '911 Publication illustrates a collection container comprising cup 502 and lid 504 connected by tubing 518 from port 516 to suction wand 520. FIG. 9 of the '911 Publication further illustrates another tube 522 that connects a suction source (not shown) to suction port 512 of the lid 504.

FIG. 10 of the '911 Publication illustrates the second lid 508 having the plunger 510 wherein the second lid 508 has been unscrewed and removed from the cup 506.

FIG. 11 of the '911 Publication illustrates that lid 508 having the plunger 510 may be screwed onto either of the two cups 502,506 of the bone press apparatus, as the cups are interchangeable.

FIG. 12 of the '911 Publication illustrates the second lid 508 screwed onto one of the cups of the bone press apparatus.

Similarly, FIG. 13 of the '911 Publication illustrates the lid 504 screwed onto one of the cups 502,506 of the bone press apparatus, and FIG. 14 of the '911 Publication illustrates the first lid 504 unscrewed and removed from the cup of FIG. 13 of the '911 Publication.

FIGS. 15-18 of the '911 Publication illustrate various views of another suction wand 620 used in preferred methods of the invention. As shown in these figures, the suction wand 620 includes a slider control 622 by which suction that is applied at suction tip 624 of the wand 620 is variably adjusted by a user.

FIG. 19 of the '911 Publication illustrates the connection of the suction wand 620 to the collection container comprising cup 502,506 and lid 504 for use in certain preferred embodiments of the invention.

FIG. 20 of the '911 Publication illustrates holding of the suction wand 620 to a collection container using suction tubing during use in certain preferred embodiments of the invention. The wand 620 is used in preferred methods by extending the suction tip thereof through a cortical window for extraction, by suction, of cancellous bone and bone marrow. The extracted cancellous bone and bone marrow is received and collected in the collection container formed by lid 504 and one of the cups 502,506 of the bone press apparatus. The suction wand 620 preferably has variable-suction control. Importantly, no irrigation is added to the bone marrow that would dilute the bone marrow and, additionally, no suction is applied during use of the press head of the plunger and the separation of the bone marrow and cancellous bone by pouring of the bone marrow into the second cup through a suction port.

Harvesting of cancellous bone and bone marrow from a tibia, femur, or cancellous bone is now described for purposes of an exemplary illustration of a preferred method in accordance with one or more aspects and features of the invention.

In particular, FIG. 21 of the '911 Publication is a perspective view of a drill 702 with burr 704 coming within proximity of cortical bone 706. FIG. 22 of the '911 Publication is a perspective view of the drill 702 being used to form a cortical opening 708 in the cortical bone 706. FIG. 23 of the '911 Publication is a perspective view of the drill 702 extended through the cortical opening 708 and being used to loosen cancellous bone and bone marrow. FIG. 24 of the '911 Publication is a perspective view of the withdrawal of the drill 702 from the opening 704. FIG. 25 of the '911 Publication is a perspective view of the apparatus of FIG. 20 of the '911 Publication being used to extract loosened cancellous bone and bone marrow through the opening 708 in the cortical bone 706. FIG. 26 of the '911 Publication is a perspective view of the approach of the suction tip 624 of the suction wand 620 to the opening 708 in the cortical bone 706. FIG. 27 of the '911 Publication is a perspective view of the extraction through suction of the loosened cancellous bone and bone marrow through the opening 708 in the cortical bone 706. FIG. 28 of the '911 Publication is another perspective view of the extraction through suction of the loosened cancellous bone and bone marrow through the opening in the cortical bone. FIG. 29 of the '911 Publication is a perspective view of the withdrawal of the apparatus of FIG. 20 of the '911 Publication from the opening 708 in the cortical bone 706. FIG. 30 of the '911 Publication is a view of the apparatus of FIG. 29 of the '911 Publication after withdrawal and after the suction source has been disconnected from the collection container. FIG. 31 of the '911 Publication is a perspective view showing the removal of the lid 504 from the cup 502,506 of the collection container and further is a perspective view of the second lid 508 with plunger and suction port 512 to be attached to the cup 502,506. FIG. 32 of the '911 Publication is a perspective view of the second lid attached to the cup and further is a perspective view of a second cup not which liquid 802 from the first cup is to be poured through the suction port of the second lid. FIG. 33 of the '911 Publication is a partial perspective view of the pouring of the liquid through the suction port of the second lid into the second cup. FIG. 34 of the '911 Publication is a perspective view of the second lid removed from the first cup, the first cup containing the spongy mass 804 of cancellous bone, and the second cup containing the liquid bone marrow 802. FIG. 35 of the '911 Publication is a perspective view showing the withdrawal and staging of the spongy mass 804 of cancellous bone from the first cup.

Figure 6:
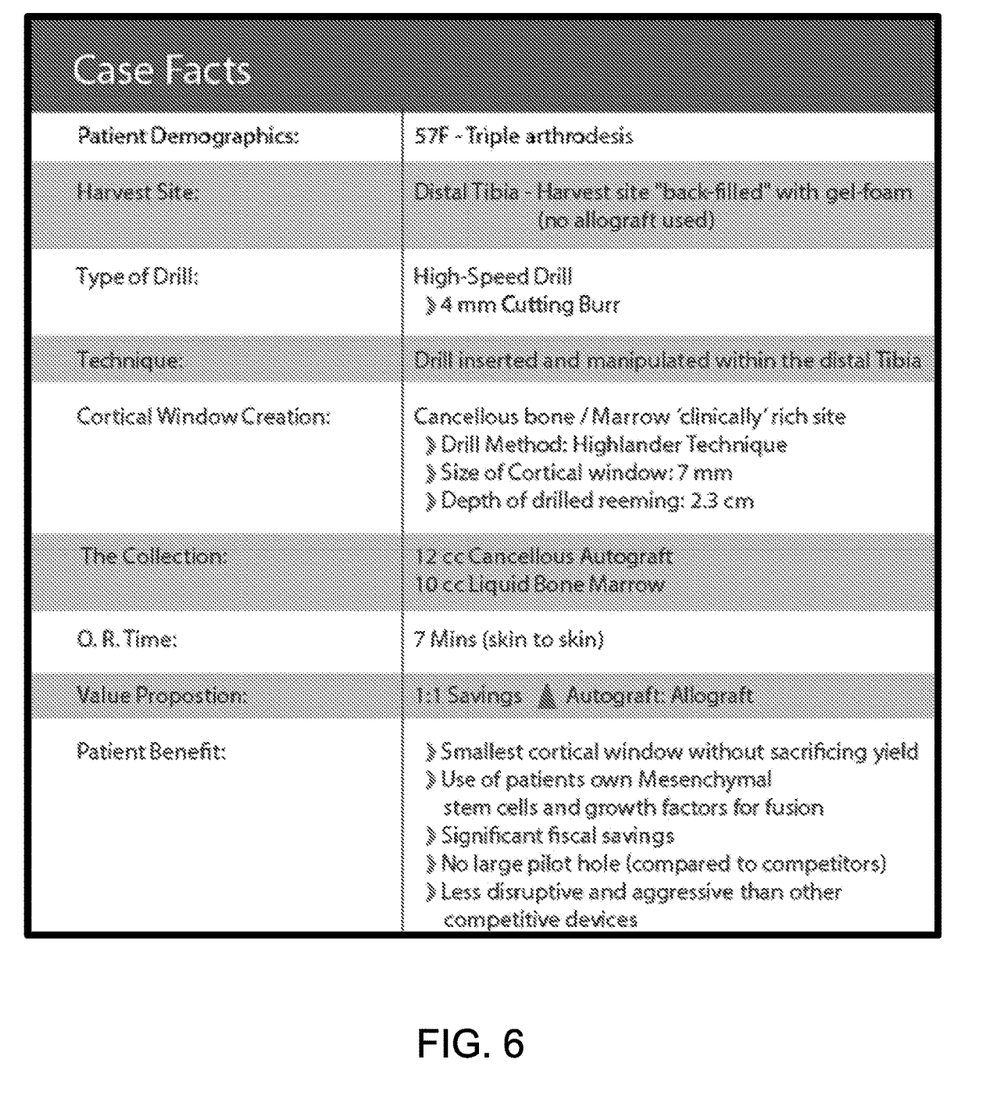
FIG. 6 is a table of case facts relating to a preferred harvesting of the invention performed in connection with the drilling and suctioning in FIGS. 6 and 7 of U.S. patent application publication 2020/0405911 ("the '911 Publication).
Figure 7:
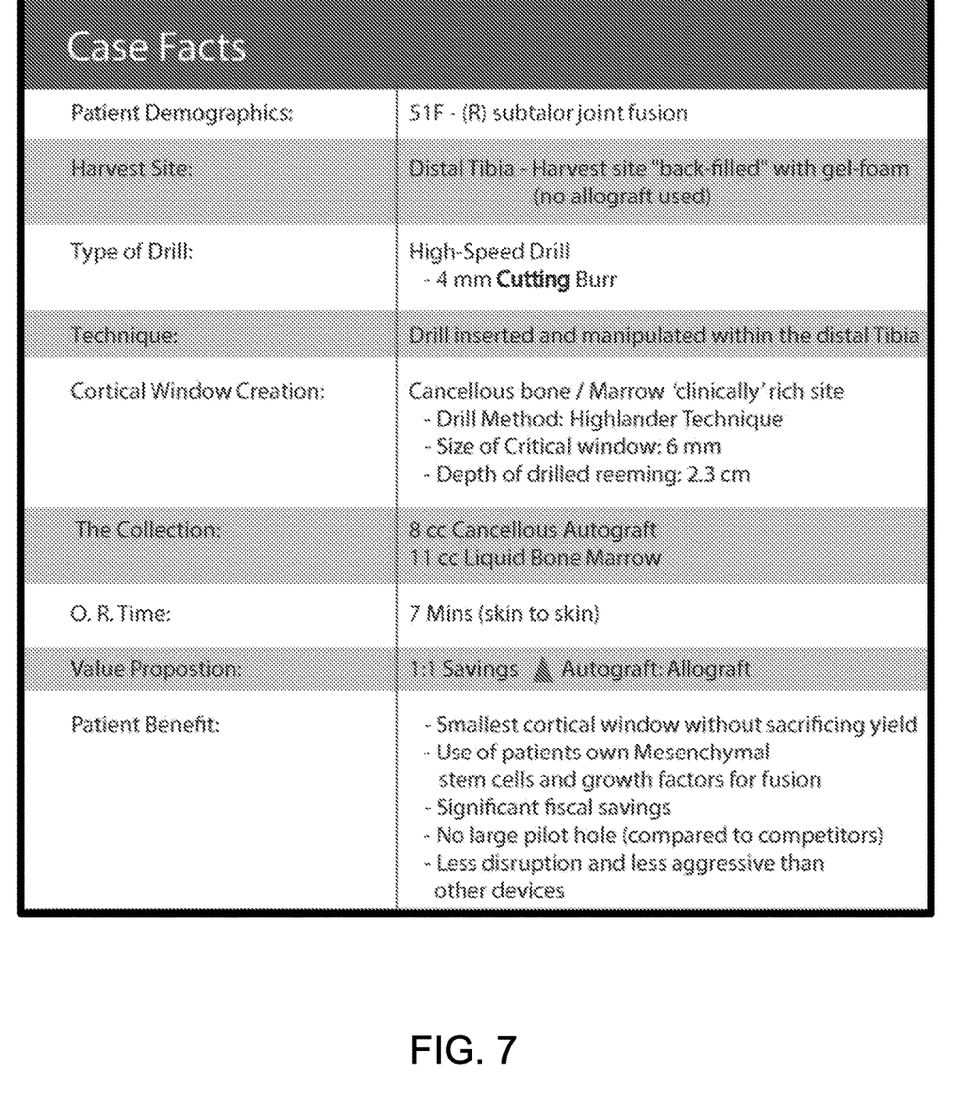
FIG. 7 is a table of case facts relating to a preferred harvesting of the invention performed in connection with the pouring and suctioning shown respectively in FIGS. 9 and 10 of the '911 Publication, the results of which are seen in FIG. 11 of the '911 Publication.

Additionally, FIG. 6 of the '911 Publication is a perspective view of drilling a cortical window in the cortical bone of the tibia in accordance with one or more aspects and features of the invention. FIG. 7 of the '911 Publication is a perspective view of the suctioning of cancellous bone and bone marrow through the cortical window created in FIG. 6 of the '911 Publication to the collection container of a bone press apparatus in accordance with one or more aspects and features of the invention. FIG. 6 is a table of case facts relating to a preferred harvesting of the invention performed in connection with the drilling and suctioning in FIGS. 6 and 7 of the '911 Publication. FIG. 9 of the '911 Publication is a perspective view of the pouring of filtered liquid from a first cup into a second cup while depressing a plunger in accordance with one or more aspects and features of the invention. FIG. 10 of the '911 Publication is a perspective view of suctioning a cancellous bone and bone marrow through a cortical window created in a tibia in accordance with one or more aspects and features of the invention. FIG. 11 of the '911 Publication is a perspective view within the first and second cups after a preferred harvesting of the invention performed in connection with the pouring and suctioning shown respectively in FIGS. 9 and 10 of the '911 Publication. FIG. 7 is a table of case facts relating to a preferred harvesting of the invention performed in connection with the pouring and suctioning shown respectively in FIGS. 9 and 10, the results of which are seen in FIG. 11.

Figure 8:
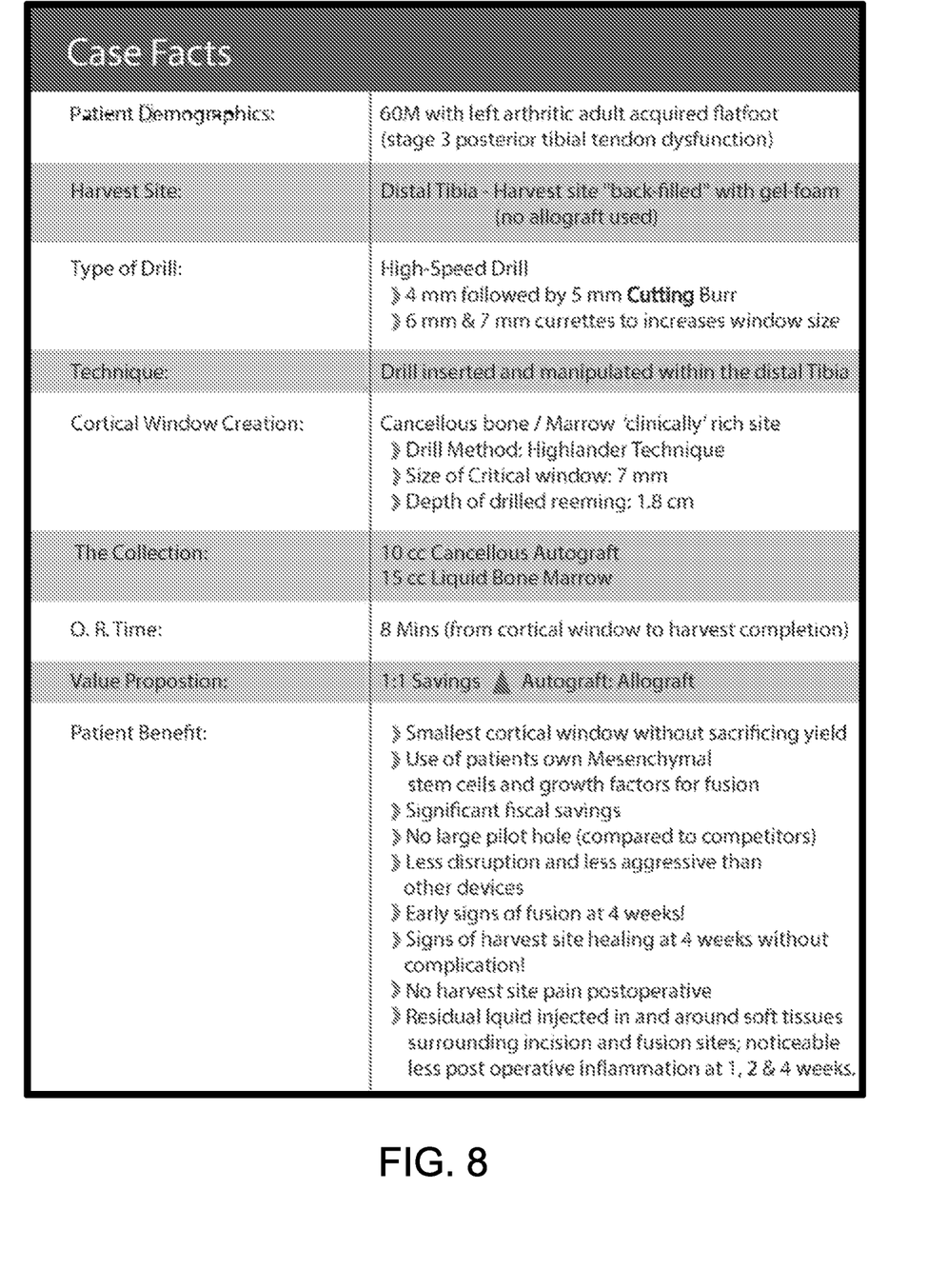
FIG. 8 is a table of case facts relating to another preferred harvesting of the invention performed in accordance with one or more aspects and features of the invention.

FIG. 8 is a table of case facts relating to another preferred harvesting of the invention performed in accordance with one or more aspects and features of the invention. FIG. 14 of the '911 Publication is a perspective view of the spongy mass of cancellous bone resulting from the preferred harvesting of FIG. 13 of the '911 Publication.

Harvesting of cancellous bone and bone marrow from an intermedullary canal is now described for purposes of an exemplary illustration of a preferred method in accordance with one or more aspects and features of the invention.

In particular, FIG. 15 of the '911 Publication is a perspective view of the drilling of a medullary cavity performed in a preferred harvesting in accordance with one or more aspects and features of the invention. FIG. 16 of the '911 Publication is a perspective view of reaming of a medullary canal following the drilling of FIG. 15 of the '911 Publication, done in the preferred harvesting in accordance with one or more aspects and features of the invention.

FIG. 17 of the '911 Publication is a view of reamers used in the reaming of FIG. 16 of the '911 Publication, showing bone on the reamers which may be harvested and combined and used with the bone that is suctioned in accordance with one or more aspects and features of the invention. FIGS. 48 to 55 of the '911 Publication are elevational views showing an exemplary creation of an intermedullary canal in accordance with one or more aspects and features of the invention, which is representative of the creation of the intermedullary canal in the preferred harvesting of FIGS. 15 and 16 of the '911 Publication done in accordance with one or more aspects and features of the invention. FIG. 18 of the '911 Publication is a perspective view showing a suction tube to be inserted into the intermedullary canal formed by the drilling and reaming respectively of FIGS. 15 and 16 of the '911 Publication done in the preferred harvesting in accordance with one or more aspects and features of the invention. FIG. 19 of the '911 Publication is a perspective view of suctioning of cancellous bone and bone marrow through the suction tube of FIG. 18 of the '911 Publication during insertion in the intermedullary canal. FIG. 20 of the '911 Publication is a perspective view of the pouring of liquid from the first cup into a second cup after the suctioning of FIG. 19 of the '911 Publication in the preferred harvesting in accordance with one or more aspects and features of the invention. FIG. 21 of the '911 Publication is a side view of the second cup following the pouring of FIG. 20 of the '911

Publication, showing liquid bone marrow that has been poured into the second cup during performance of the preferred harvesting in accordance with one or more aspects and features of the invention. FIG. 9 is a table of case facts relating to the preferred harvesting of the invention performed in connection with the drilling, reaming, inserting, suctioning, and pouring shown respectively in FIGS. 15, 16, 18, 19, and 20 of the '911 Publication.

As a result of the methods disclosed herein utilizing the bone press apparatus with the suction for collecting both cancellous bone and bone marrow and then separating the bone marrow from the cancellous bone using the press head of the plunger, it has been discovered that an unexpectedly large yield of cancellous bone and bone marrow is obtained following intramedullary reaming. From actual implementation, 20 cc and more of cancellous bone and 20 cc and more of bone marrow have been obtained following traditional intramedullary reaming procedures used in connection for an intramedullary nail or rod.

In recap of FIGS. 45-60 of the '911Publication., which subsume FIGS. 15-17 of the '911 Publication, and 18-22 of the '911 Publication hereof, preferred methods of the invention include harvesting cancellous bone and marrow from an intramedullary canal of an individual for use as an autograft for that individual following drilling and reaming. An exemplary method is now set forth. In particular, a long pilot hole is created by a drill within the center of a long bone such as the tibia. Drilling and intramedullary reaming loosens up the cancellous bone and marrow. Preferably, an intramedullary rod is inserted into the canal afterwards. Once depth of drilling to create the intramedullary canal is satisfactory for the surgeon, the reamer is used. The reamer is cannulated whereby the guide wire remains within the canal the entire time. Multiple reamers are used and set aside for keeping the bone to be added to the press later. The bone captured on the reamers is scraped off with an instrument and used in the autograft. Once the reaming is complete, the bone press apparatus with suction is employed. A suction line is cut approximately 2-3 feet and attached to the silicon tubing. The tubing can be cut and the new suction tubing can be placed over the superior port, but this is not necessary, as the bone press apparatus preferably has a right angle for connecting the tubes. With suction on, the cut suction line is inserted around the guide wire. The guide wire does not leave the canal. Then by moving the suction tubing all the way in and spinning the tubing in multiple in and out motions within the canal and over the guide wire, cancellous bone and marrow is harvested from the medullary cavity along the intramedullary canal created by the intramedullary reaming. Once done, the collection is handed off to the scrub tech and the press top is attached. Of note, suction is not applied when the press head is used. Instead, the plunger is fully pressed downward and the apparatus tilted to pour off the liquid marrow into a second container. Of note, suction is not applied when the press head is used. Instead, the plunger is fully pressed downward and the apparatus tilted to pour off the liquid marrow into a second container that is part of the bone press apparatus.

Based on the foregoing description, it will be readily understood by those persons skilled in the art that the invention has broad utility and application. Many embodiments and adaptations of the invention other than those specifically described herein, as well as many variations, modifications, and equivalent arrangements, will be apparent from or reasonably suggested by the invention and the foregoing descriptions thereof, without departing from the substance or scope of the invention. Accordingly, while the invention has been described herein in detail in relation to one or more preferred embodiments, it is to be understood that this disclosure is only illustrative and exemplary of the invention and is made merely for the purpose of providing a full and enabling disclosure of the invention. The foregoing disclosure is not intended to be construed to limit the invention or otherwise exclude any such other embodiments, adaptations, variations, modifications or equivalent arrangements, the invention being limited only by the claims appended hereto and the equivalents thereof.

What is claimed is:

1. A method of harvesting cancellous bone and bone marrow, comprising:
   (a) creating an opening in cortical bone;
   (b) accessing through the opening and loosening for extraction cancellous bone and bone marrow;
   (c) inserting a suction apparatus through the opening and extracting the loosened cancellous bone and bone marrow, the bone marrow comprising a liquid, the suction apparatus being attached to a first lid of a collection container, the collection container having a suction port to which a suction source is connected;
   (d) after extracting the cancellous bone and bone marrow, disconnecting the suction source from the suction port of the collection container;
   (e) removing the first lid of the collection container from a first cup of the collection container;
   (f) attaching a second lid to the first cup of the collection container, the second lid having a plunger with a press head configured to filter the extracted liquid contained in the first cup;
   (g) filtering the extracted liquid by depressing the plunger of the second lid toward a bottom of the first cup; and
   (h) pouring the filtered liquid from the first cup through a suction port into a second cup while depressing the plunger, thereby separating the liquid from a spongy semi-solid mass of cancellous bone that remains in the first cup.

2. The method of claim 1, wherein the suction apparatus comprises a suction wand.

3. The method of claim 2, wherein extracting the loosened cancellous bone and bone marrow comprises sweeping a distal end of the suction wand in various directions while extracting the loosened cancellous bone and bone marrow.

4. The method of claim 3, wherein the sweeping step is performed while holding the collection container to which the suction apparatus is attached.

5. The method of claim 1, further comprising pouring or drawing the filtered liquid from the second cup into a syringe and injecting the liquid within an autograft or directly into an operative site to promote healing.

6. The method of claim 1, further comprising leaving the suction apparatus attached to the first lid for repeating the harvesting method.

7. The method of claim 1, wherein no irrigation is performed that would dilute the extracted liquid.

8. The method of claim 1, wherein no suction is applied to the first cup during depressing of the plunger.

9. The method of claim 1, wherein the second lid having the plunger additionally comprises a vent, whereby a low pressure is not created within the first cup during pouring of the liquid through the suction port while depressing the plunger.

10. The method of claim 1, wherein the step of creating an opening in cortical bone comprises using a high-speed drill having a cutting burr to create the opening.

11. The method of claim 10, wherein the cutting burr is used to create the opening and to loosening the cancellous bone and bone marrow for extraction that is accessed through the opening.

12. The method of claim 1, wherein the step of creating an opening in cortical bone comprises using a drill comprising a 4 mm cutting burr followed by replacing the 4 mm cutting burr with a 5 mm cutting burr and continuing to use the drill.

13. The method of claim 12, further comprising the steps of using 6 mm and then 7 mm currettes to increase the size of the opening.

14. The method of claim 12, wherein a maximum dimension of the opening created using the drill is approximately 6 mm to 7 mm.

15. The method of claim 12, wherein a depth of drilling is between 1.8 cm to 2.3 cm inclusive.

16. A method of harvesting from an individual, in an operating room and within 8 minutes, at least 8 cc to 12 cc of a spongy semi-solid mass of cancellous bone of the individual and, separated therefrom, at least 10 cc to 15 cc of liquid bone marrow of the individual, the method comprising:
   (a) using a high-speed drill having a cutting burr to create a cortical window in cortical bone;
   (b) further using the high-speed drill to loosen for extraction cancellous bone and bone marrow accessed through the cortical window;
   (c) inserting a suction apparatus through the cortical window and extracting the loosened cancellous bone and bone marrow, the bone marrow comprising a liquid, the suction apparatus being attached to a first lid of a collection container, the collection container having a suction port to which a suction source is connected;
   (d) after extracting the cancellous bone and bone marrow, disconnecting the suction source from the suction port of the collection container;
   (e) removing the first lid of the collection container from a first cup of the collection container;
   (f) attaching a second lid to the first cup of the collection container, the second lid having a plunger with a press head configured to filter the extracted liquid contained in the first cup;
   (g) filtering the extracted liquid by depressing the plunger of the second lid toward a bottom of the first cup; and
   (h) pouring the filtered liquid from the first cup through a suction port into a second cup while depressing the plunger, thereby separating the liquid from a spongy semi-solid mass of cancellous bone that remains in the first cup.

17. The method of claim 16, wherein the cortical window is created in cortical bone at a distal tibia.

18. The method of claim 16, wherein the cortical window is created in cortical bone at a distal femur.

19. The method of claim 16, wherein the cortical window is created in cortical bone at a proximal tibia.

20. The method of claim 16, wherein the cortical window is created in cortical bone at a calcaneus.

* * * * *